(12) United States Patent
Dhindsa (10) Patent No.: US 6,786,865 B2
(45) Date of Patent: Sep. 7, 2004

(54) ENDOSCOPE VALVE ASSEMBLY AND METHOD

(75) Inventor: Avtar S. Dhindsa, Valparaiso, IN (US)

(73) Assignee: Innon Holdings, LLC, Valparaiso, IN (US)

(*) Notice: Subject to any disclaimer, the term of this patent is extended or adjusted under 35 U.S.C. 154(b) by 0 days.

(21) Appl. No.: 10/271,485

(22) Filed: Oct. 16, 2002

(65) Prior Publication Data

US 2004/0010183 A1 Jan. 15, 2004

Related U.S. Application Data

(63) Continuation-in-part of application No. 10/022,134, filed on Dec. 12, 2001, now Pat. No. 6,666,818, which is a continuation-in-part of application No. 09/761,784, filed on Jan. 17, 2001, now Pat. No. 6,533,720.

(51) Int. Cl.$^7$ ................................................. A61B 1/12
(52) U.S. Cl. ........................ 600/159; 600/158; 600/156
(58) Field of Search ................................ 600/105, 131, 600/135, 153, 156, 158, 157

(56) References Cited

U.S. PATENT DOCUMENTS

| | | |
|---|---|---|
| 591,228 A | 10/1897 | Gotermann |
| 1,668,865 A | 5/1928 | Nelson |
| 2,691,370 A | 10/1954 | Wallace |
| 3,027,913 A | 4/1962 | Chatham et al. |
| 3,144,020 A | 8/1964 | Zingale |
| 3,765,447 A | 10/1973 | Cornell |
| 3,791,379 A | 2/1974 | Storz |
| 4,132,227 A | 1/1979 | Ibe |

(List continued on next page.)

FOREIGN PATENT DOCUMENTS

WO WO 02/056942 A2 7/2002

OTHER PUBLICATIONS

"Pathfinder Plus Continuous and Pulsatile Irrigation Bulb," Utah Medical Products, 1 page, Jan. 5, 1999.
"Utah Medical Products Inc., Pathfinder Plus, An Advancement in Physician Controlled Irrigation, Pathfinder Plus Endoscopic Surgical Irrigators," http://www.utahmed.com/pathfind.htm, 2 pages, Apr. 19, 2000.
"Utah Medical Products Inc., Pathfinder Plus Specifications," http://www.utahmed.com/pathfnds.htm, 1 page, Apr. 19, 2000.
"Now All You Need is the Perfect Valve," B. Braun Medical Inc., 1 page, 2001.
"Distortion–Free Hydro Laparoscopes with Distal Lens Warming," Circon Corporation, p. L–7, (undated).
"Corson Suction–Irrigation Probes 005200–903," Circon Corporation, 2 pages, 2000.
"Opti4 Laparoscopic Handset and Electrodes," http://www.valleylab.com/displayproduct.cfm?productid=128&menu=product, 1 page, 2002.
Photographs of "Opti4 Laparoscopic Handset and Electrodes" showing interior mechanisms, 2 pages (photos taken May 2002).
"Modular Endoscope Valve Assembly and Method," U.S. patent application Ser. No. 09/761,784, filed Jan. 17, 2001; inventor: Avtar S. Dhindsa.

*Primary Examiner*—Beverly M. Flanagan
(74) *Attorney, Agent, or Firm*—Brinks Hofer Gilson & Lione (57) ABSTRACT

In one embodiment, an endoscope valve assembly is releasably secured to a hand of a user of an endoscope. The endoscope valve assembly can be releasably secured to any part of the user's hand (e.g., palm, thumb, or finger) and can be secured either to the hand that holds the endoscope or to the user's other hand. Additionally, when the user holds an endoscope in one hand and a second medical instrument in his other hand, the valve assembly for the endoscope can be releasably secured to the second medical instrument. Other embodiments are described, and each of the embodiments can be used alone or in combination with each other.

46 Claims, 8 Drawing Sheets

U.S. PATENT DOCUMENTS

| | | |
|---|---|---|
| 4,284,101 A | 8/1981 | Weirich |
| 4,497,468 A | 2/1985 | Hubbard et al. |
| 4,535,919 A | 8/1985 | Jameson |
| 4,557,255 A | 12/1985 | Goodman |
| 4,567,880 A | 2/1986 | Goodman |
| 4,572,163 A | 2/1986 | Collins et al. |
| 4,874,066 A | 10/1989 | Silberstein |
| 4,881,523 A | 11/1989 | Heckele |
| 5,020,514 A | 6/1991 | Heckele |
| 5,064,168 A | 11/1991 | Raines et al. |
| 5,125,910 A | 6/1992 | Freitas |
| 5,201,908 A | 4/1993 | Jones |
| 5,207,213 A | 5/1993 | Auhll et al. |
| 5,228,646 A | 7/1993 | Raines |
| 5,290,279 A | 3/1994 | Bonati et al. |
| 5,324,254 A | 6/1994 | Phillips |
| 5,447,148 A | 9/1995 | Oneda et al. |
| 5,483,991 A | 1/1996 | D'Agostino et al. |
| 5,536,234 A | 7/1996 | Newman |
| 5,647,840 A | 7/1997 | D'Amelio et al. |
| 5,792,139 A | 8/1998 | Chambers et al. |
| 5,830,126 A | 11/1998 | Odanaka et al. |
| 5,913,816 A | 6/1999 | Sanders et al. |
| 5,944,654 A | 8/1999 | Crawford |
| 5,967,179 A | 10/1999 | Kazakis et al. |
| 6,383,132 B1 | 5/2002 | Wimmer |

ENDOSCOPE VALVE ASSEMBLY AND METHOD

CROSS REFERENCE TO RELATED APPLICATIONS

This application is a continuation-in-part of U.S. patent application Ser. No. 10/022,134, filed Dec. 12, 2001, now U.S. Pat. No. 6,668,818 which is a continuation-in-part of U.S. patent application Ser. No. 09/761,784, filed Jan. 17, 2001 now U.S. Pat. No. 6,533,720. Both applications are hereby incorporated by reference in their entirety.

BACKGROUND

The present invention relates to endoscopic surgical devices, and in particular to valve assemblies used to control the flow of irrigation fluid in such devices.

Endoscopic devices are customarily provided with an irrigation port that conducts an irrigation liquid to the viewing area at the end of the endoscopic device. One prior-art approach is to pressurize irrigation fluid in an IV fluid bag, and then to supply the pressurized irrigation fluid directly into an endoscope such as a ureteroscope. The endoscope includes integral valves that are generally operated with one hand while the other hand holds the handpiece of the endoscope. The advantage of this system is that the irrigation fluid is pressurized, thereby providing dilation of a ureter and good visibility. One potential disadvantage with this type of irrigating system is that it may be difficult to control fluid flow since two hands are required. If the fluid flow is not controlled properly, a stone can be dislodged back into the middle or upper ureter by an excessively high rate of flow. Also, In the event of extravasation, uncontrolled amounts of fluid can flow into the retroperitoneum.

Another type of irrigation system is a hand-operated, pressurized irrigating system commercially manufactured by Bard, Boston Scientific, and ACMI. This approach allows the amount of fluid being injected to be controlled, but the apparatus is relatively bulky. This system is mounted separately from the ureteroscope, and separate hands are used to hold the handpiece of the ureteroscope and to control the flow of irrigation fluid. On occasion, an assistant controls fluid flow while the physician holds the endoscope in the left hand and performs an endoscopic procedure with the right hand. In this case, precise control of the rate of fluid flow is difficult, because oral instructions are slower and less precise than direct manual control by the physician.

A third type of irrigation system includes two or more syringes that are operated by an assistant one at a time to supply pressurized irrigation fluid to the endoscopic device. Generally a valve is provided that allows the assistant to fill one of the syringes while the other is in use.

A fourth type of irrigation system includes a roller pump mechanism that delivers irrigation fluid at a constant set pressure. This system may incorporate a blow-off valve to prevent excessive pressure, and it is generally used in endoscopic specialties such as orthopedics in performing arthroscopies. This system requires the use of an electric motor and controller, and it is therefore costly and bulky.

Goodman U.S Pat. No. 4,567,880 discloses an endoscopic device having a three-way valve forming a permanent portion of the handpiece of the endoscope. This system allows a physician to control the flow of irrigation fluid with the same hand as that used to hold the handpiece. However, the Goodman system requires a specially constructed endoscope, and the irrigation system is an Integral part of the endoscope. This limits the irrigation system to use with one particular endoscope.

The present invention is directed to an improved system and method for controlling the flow of irrigation fluid in an endoscopic device.

SUMMARY

The present invention is defined by the following claims, and nothing in this section should be taken as a limitation on those claims.

By way of introduction, the preferred embodiments described below provide an endoscope valve assembly and method. In one embodiment, an endoscope valve assembly is releasably secured to a hand of a user of an endoscope. The endoscope valve assembly can be releasably secured to any part of the user's hand (e.g., palm, thumb, or finger) and can be secured either to the hand that holds the endoscope or to the user's other hand. Additionally, when the user holds an endoscope in one hand and a second medical instrument in his other hand, the valve assembly for the endoscope can be releasably secured to the second medical instrument. Other embodiments are described, and each of the embodiments can be used alone or in combination with each other.

The embodiments will now be described with reference to the attached drawings.

DETAILED DESCRIPTION OF THE PRESENTLY PREFERRED EMBODIMENTS

Figures 1, 2, 3:
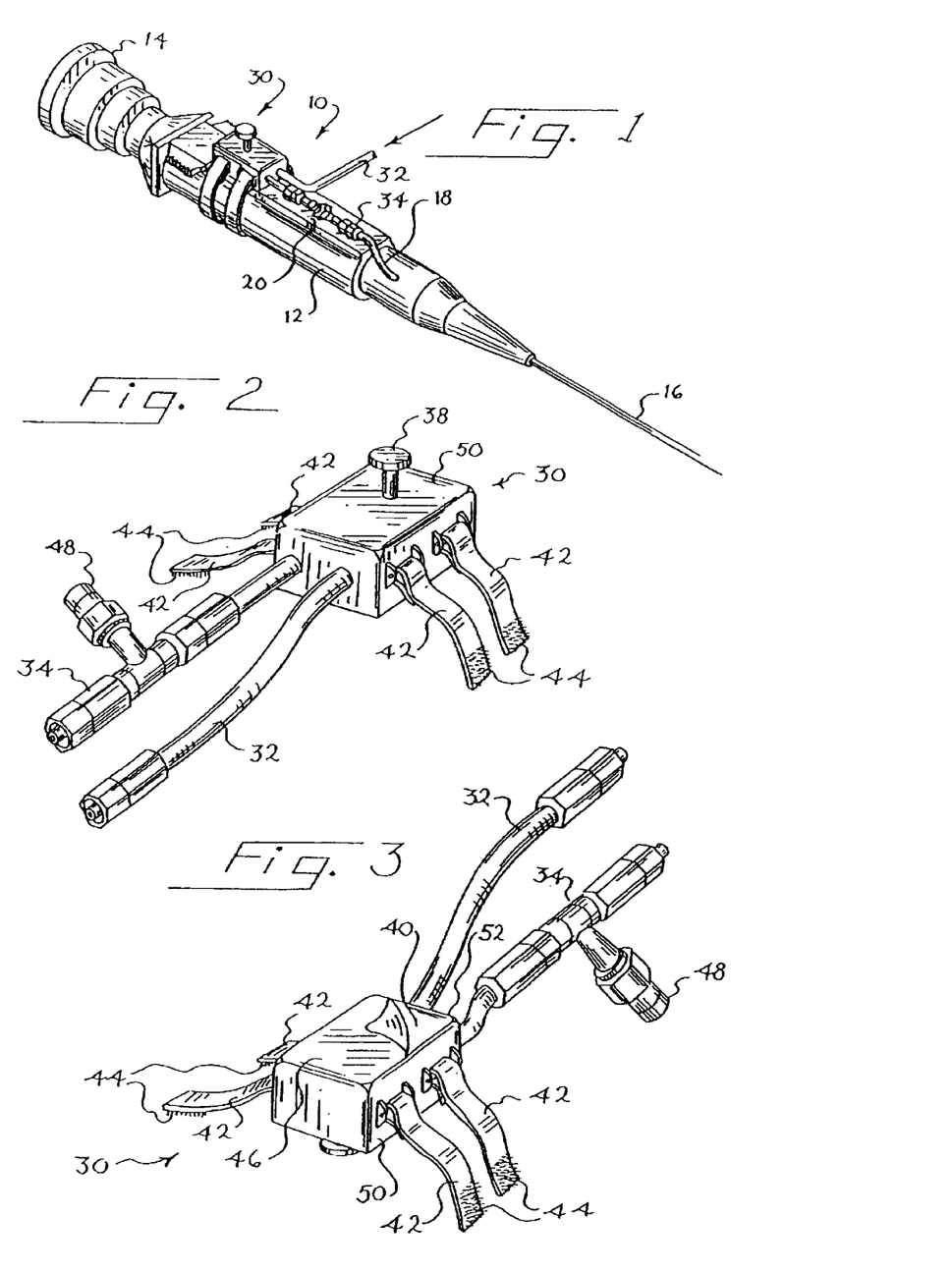
FIG. 1 is a perspective view of a ureteroscope on which is mounted a modular valve assembly.
FIG. 2 is a top perspective view of the valve assembly of FIG. 1, prior to mounting on the ureteroscope.
FIG. 3 is a bottom perspective view of the valve assembly of FIG. 2.

Turning now to the drawings, FIG. 1 is a perspective view of an endoscopic device 10 that in this embodiment is a ureteroscope. The ureteroscope 10 includes a handpiece 12 that carries an eyepiece 14 at one end and a shaft 16 at the other end. An irrigation port 18 is carried by the handpiece 12, and irrigation fluid introduced via the Irrigation port 18 is conducted to the viewing area at the end of the shaft 16 that is inserted into the patient. The handpiece 12 also defines an exterior surface 20.

The endoscopic device 10 can take any suitable form, and the present invention is not limited to any particular embodiment. For example, the endoscopes of any of the following U.S Patents can be adapted for use with this invention: Wallace U.S. Pat. No. 2,691,370, Ibe U.S. Pat. No. 4,132,227, Goodman U.S. Pat. No. 4,567,880, Cho U.S. Pat. No. 5,083,549, Muller U.S. Pat. No. 5,199,417, Bonati U.S. Pat. No. 5,290,279, and Odanacka U.S. Pat. No. 5,830,126. Conventional endoscopes such as the ureteroscopes manufactured by ACMI, Wolf, Olympus and Storz are also well-adapted for use with this invention. This list is Intended only by way of illustration, in the widest variety of ureteroscopes, arthroscopes, laparoscopes, hysteroscopes, sinuscopes, and endoscopes adapted for other specialties can be used with this invention, including flexible, semi-rigid, and rigid endoscopes.

In use, the physician holds the handpiece with one hand, thereby presenting the eyepiece for viewing and positioning the shaft as desired. The other hand is typically used to manipulate surgical tools introduced into the patient via the working port on the shaft. As shown in FIG. 1, a modular endoscope valve assembly 30 is releasably secured to the handpiece 12. This valve assembly 30 is shown in greater detail in FIGS. 2 and 3, and it includes an inlet port 32 and an outlet port 34. In use the inlet port 32 is releasably connected to a source of pressurized irrigation fluid, and the outlet port 34 is releasably connected to the irrigation port 18 of the handpiece.

The valve assembly 30 includes a valve that is interposed between the inlet port 32 and the outlet port 34 and is controlled by a valve actuator 38. The valve assembly 30 also includes a housing 50 that includes a mounting surface 52. The mounting surface 52 carries a pressure-sensitive adhesive 40 initially covered by a release paper 46. The housing 50 also supports a pair of straps 42 that include respective hook-and-loop fasteners 44. A contrast-introduction port 48 is provided in fluid communication with the outlet port 34. Check valves, not shown, can be provided to prevent flow from the outlet port 34 to the contrast-introduction port 48 and vice-versa.

Figures 4, 5, 6, 7, 8:
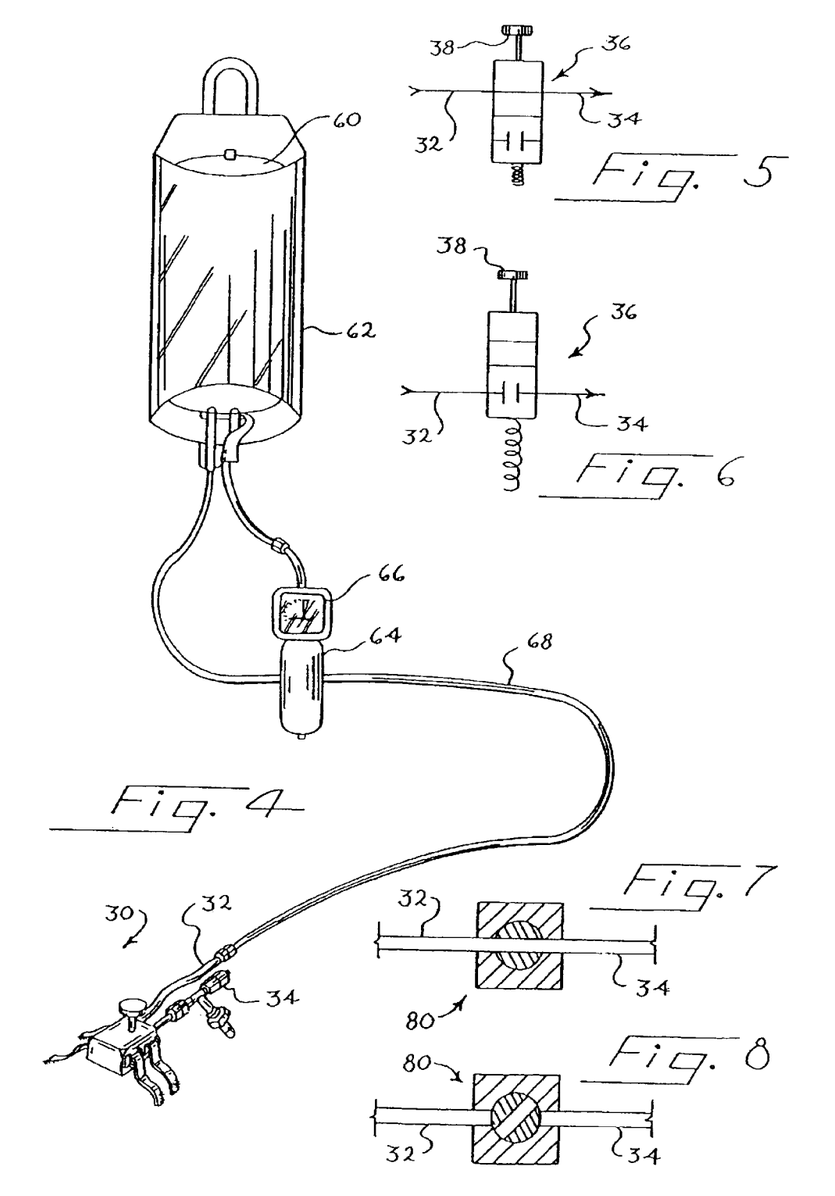
FIG. 4 is a perspective view of the valve assembly of FIGS. 2 and 3 connected to a source of pressurized irrigation fluid.
FIGS. 5 and 6 are schematic views showing the valve of the valve assembly of FIGS. 1–3 in the opened and closed positions, respectively.
FIGS. 7 and 8 are schematic views of an alternative, rotary-motion valve in the opened and closed positions, respectively.

FIG. 4 shows the manner in which the inlet port 32 of the valve assembly 30 can be releasably connected to a source of pressurized irrigation fluid, in this case contained within an IV bag 60. The IV bag 60 is disposed within a pressure cuff 62 that can be inflated with an inflator 64 to a pressure indicated by a pressure gauge 66. Standard Luer-lock fittings can be used to connect the inlet port 32 to a tube 68 that is in turn connected to the IV bag 60. The IV bag contains a conventional irrigation fluid, which is pressurized by inflating the pressure cuff 62 to a desired pressure with the inflator 64.

FIGS. 5 and 6 show two schematic views of the valve 36 of the valve assembly 30. In FIG. 5 the valve actuator 38 is depressed and the valve 36 allows fluid flow from the inlet port 32 to the outlet port 34. When manual pressure is removed from the valve actuator 38, the valve 36 returns to the position of FIG. 6, in which the valve 36 blocks the flow of fluid between the inlet and the outlet ports 32, 34. Alternatively, the valve 38 may be arranged such that fluid flow is blocked when the actuator 38 is depressed and unblocked when the actuator 38 is released.

The valve 36 of FIGS. 5 and 6 is a linear valve that slides along a linear axis between the opened position of FIG. 5 and the closed position of FIG. 6. Other types of valves are suitable, including the linear valve of U.S. Pat. No. 4,238,108 and the rotary valve 80 of FIGS. 7 and 8. A rotary valve 80 rotates about an axis between the opened position of FIG. 7 and the closed position of FIG. 8, and the associated valve actuator (not shown in FIGS. 7 and 8) moves in a rotary motion as well.

In use, the valve assembly 30 is distributed separately from the endoscope 10. In this embodiment, the valve assembly 30 is shaped to fit on a wide variety of endscopes 10 such that the endoscope 10 does not have to be specially shaped or configured for the valve assembly 30. Prior to an endoscopic procedure, the release paper 46 is removed, thereby exposing the pressure-sensitive adhesive 40 on the mounting surface 52. Then the valve assembly 30 is placed on the exterior surface 20 of the endoscope 10, and the pressure-sensitive adhesive 40 releasably holds the valve assembly 30 in place. The straps 42 are positioned around the handpiece 12, and the hook-and-loop fasteners 44 are secured together to hold the valve assembly 30 in place.

Either before or after the valve assembly 30 is secured to the handpiece 12, the inlet port 32 is releasably secured to the tube 68 (FIG. 4) and the outlet port 34 is releasably secured to the irrigation port 18 of the handpiece 12 (FIG. 1). Preferably, the valve assembly 30 is flushed after it is connected to the tube 68 and before it is connected to the irrigation port 18.

The physician then performs the desired endoscopic procedure, using a single hand both to hold the handpiece 12 and to control the flow of pressurized irrigation fluid with the valve assembly 30. A part of the hand that holds the handpiece (e.g. the fingers or the heel) is used to move the valve actuator.

Once the endoscopic procedure has been completed, the valve assembly 30 can simply be removed from the endoscope 10 by releasing the hook-and-loop fasteners 44 and lifting or twisting the valve assembly 10 away from the handpiece 12 until the pressure-sensitive adhesive 40 releases.

The valve assembly 30 described above uses both a pressure-sensitive adhesive and a set of straps to releasably secure the valve assembly 30 in place on the handpiece 12. In alternative embodiments the adhesive may be used without the reinforcing straps, or the reinforcing straps can be used without the adhesive. The strap may be varied widely.

For example, the strap may pass over the top of the valve assembly, and the actuator may pass through an opening in the strap. The strap may be fixed to the valve assembly or not. Also, other types of fasteners can be used to releasably hold the valve assembly in place on the endoscope.

Figure 9:
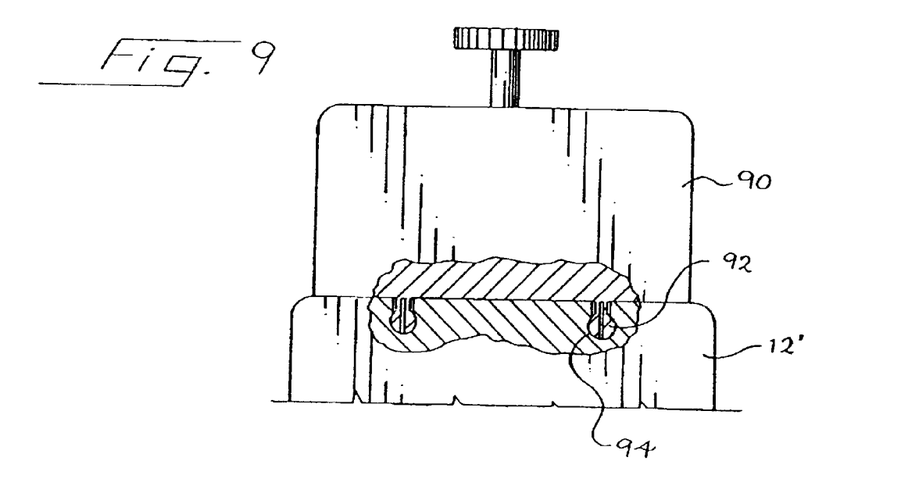
FIG. 9 is a fragmentary sectional view of another modular valve assembly of this invention mounted on a ureteroscope.

FIG. 9 shows a second preferred embodiment 90 of the modular valve assembly of this invention. The valve assembly 90 is identical to the valve assembly 30 described above except for the manner of releasably attaching the valve assembly 90 to the handpiece 12'. In this case the valve assembly 90 is provided with mechanical fasteners 92 and the handpiece 12' is provided with mating mechanical fasteners 94 such that the valve assembly 90 can be snapped in place on the handpiece 12' and removed from the handpiece 12' as desired. In this example, the fasteners 92 take the form of protruding studs and the mating fasteners 94 take the form of recesses shaped to receive the fasteners 92 in a snap-lock action.

Figure 10:
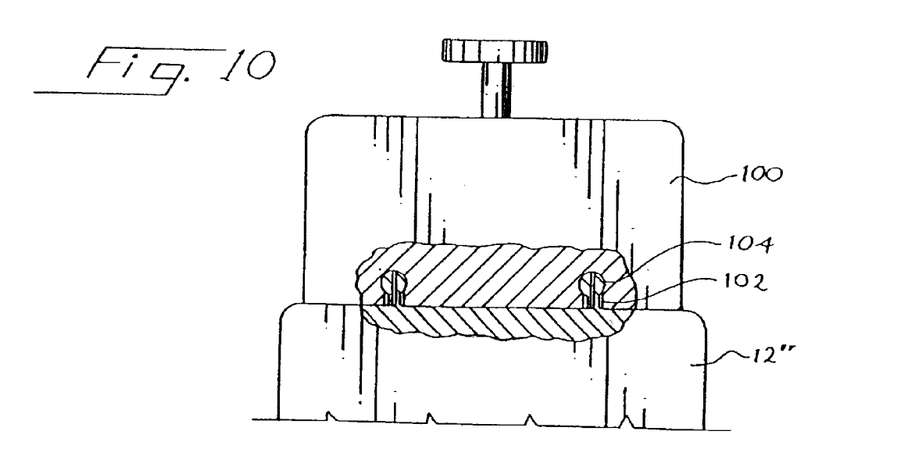
FIG. 10 is a fragmentary sectional view of yet another modular valve assembly of this invention.

FIG. 10 shows portions of a third valve assembly 100 which is similar to that of FIG. 9 except that the fasteners 102 are shaped as recesses and the mating fasteners 104 are shaped as protruding studs that fit into the fasteners 102 in a snap-lock manner.

Figure 11:
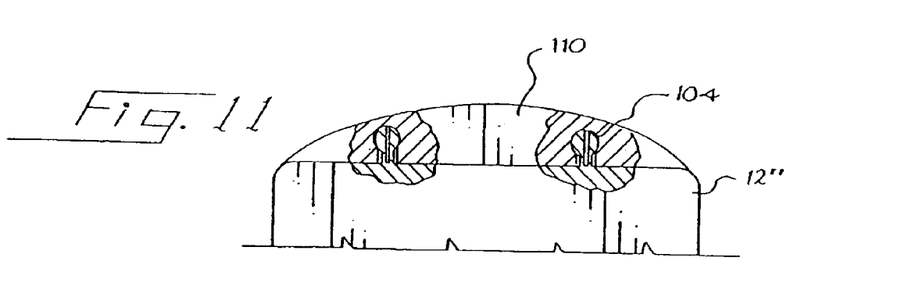
FIG. 11 is a fragmentary sectional view of the ureteroscope of FIG. 10 and a cover plate.

FIG. 11 shows the handpiece 12" of FIG. 10 with a cover 110 snapped in place on the mating fasteners 104. The cover 110 covers the mating fasteners 104 when a valve assembly is not in place on the handpiece 12".

Figure 12:
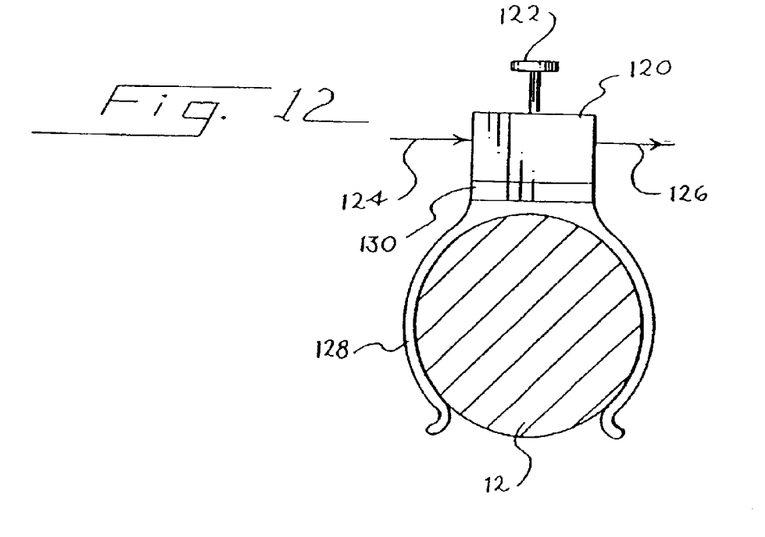
FIG. 12 is a fragmentary sectional view of another modular valve assembly of this invention mounted on a ureteroscope.

FIG. 12 shows another modular valve assembly 120 mounted in place on the handpiece 12 of an endoscopic device. The valve assembly 120 includes an actuator 122, an inlet port 124, and an outlet port 126. The valve assembly 120 is mounted on a base 130, and the base 130 supports a spring clip 128 that is designed to fit at least partially around the handpiece 12 and to releasably hold the base 130 and therefore the valve assembly 120 in position on the handpiece 12. The spring clip 128 is another example of a mechanical fastener that is suitable for releasably securing a modular valve assembly to an endoscopic device. In this example, the outer surface of the handpiece 12 can be considered a mating fastener that cooperates with the spring clip 128 to releasably hold the valve assembly 120 in place on the endoscopic device. The details of construction of the modular valve assembly 120 can be varied widely, in accordance with any of the other valve assemblies described in this specification.

Figure 13:
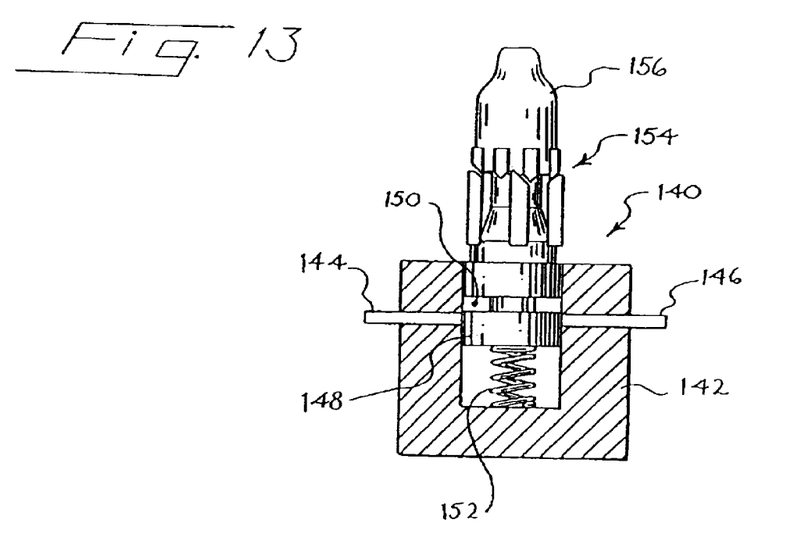
FIG. 13 is a cross-sectional view of another modular valve assembly of this invention including a mechanical latch to hold the valve in a selected position.

FIG. 13 provides a sectional view of another modular valve assembly 140. The modular valve assembly 140 includes a housing 142 that supports an inlet port 144 and an outlet port 146. A valve element 148 is slidably received in a cylinder defined by the housing 142, and the valve element 148 defines an annular recess 150. The annular recess 150 completely encircles the valve element 148, and thereby provides an interconnecting flow path between the inlet port 144 and the outlet port 146 when the recess 150 is aligned with the ports 144,146. The valve element 148 is biased to the upper position shown in FIG. 13 by a spring 152. The valve assembly 140 includes an actuator 156 that can be pressed downwardly by a finger of the user. A latch 154 is interposed between the actuator 156 and the valve element 148, and the latch 154 operates to hold the valve element 148 in a selected position.

In use, the inlet port 144 is coupled to a source of irrigation fluid and the outlet port 146 is coupled to the irrigation port of an endoscopic device. In the position shown in FIG. 13, the recess 150 is out of alignment with the inlet and outlet ports 144, 146, and no irrigation fluid is passed to the outlet port 146. When the user presses the actuator 156 downwardly in the view of FIG. 13, the recess 150 comes into alignment with the inlet and outlet ports 144, 146, thereby permitting irrigation liquid to flow to the endoscopic device. Further downward movement of the actuator 156 causes the latch 154 to hold the valve element 148 in a position in which the recess 150 is aligned with the inlet and outlet ports 144, 146. Once the latch 154 is engaged, the user can take his or her hand off of the actuator 156, and high volume flow of irrigation fluid is maintained from the inlet port 144 to the outlet port 146.

In order to stop the flow of irrigation fluid, the user again depresses the actuator 156, thereby causing the latch 154 to release the valve element 148 to move upwardly, back to the position of FIG. 13.

The valve assembly 140 allows the user to modulate the flow of irrigation fluid as described above as he or she gradually depresses the actuator 156. The latch 154 also allows the user to latch the valve in the open position, until it is released by the user.

Many alternative structures can be used for the latch 154. For example, the latch 154 can be constructed like the latch mechanism conventionally used with retractable ballpoint pens. Such latch mechanisms respond to first depression of the actuator by latching the latched element down, and they respond to a next depression of the actuator by allowing the latched element to move upwardly. This is only one example, and many alternatives are possible.

Figure 14:
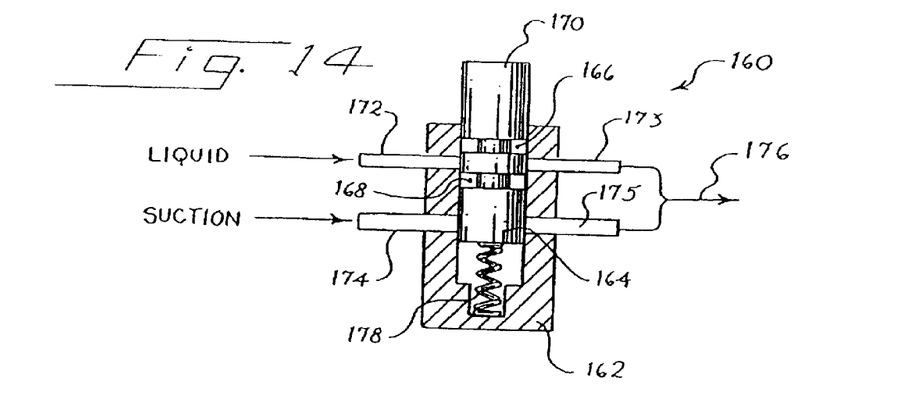
FIGS. 14, 15 and 16 are three sectional views of another modular valve assembly of this invention in three different positions.
Figure 15:
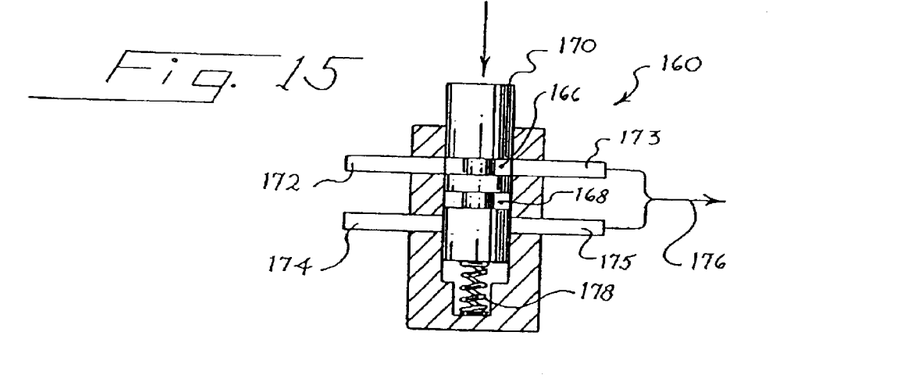
Figure 16:
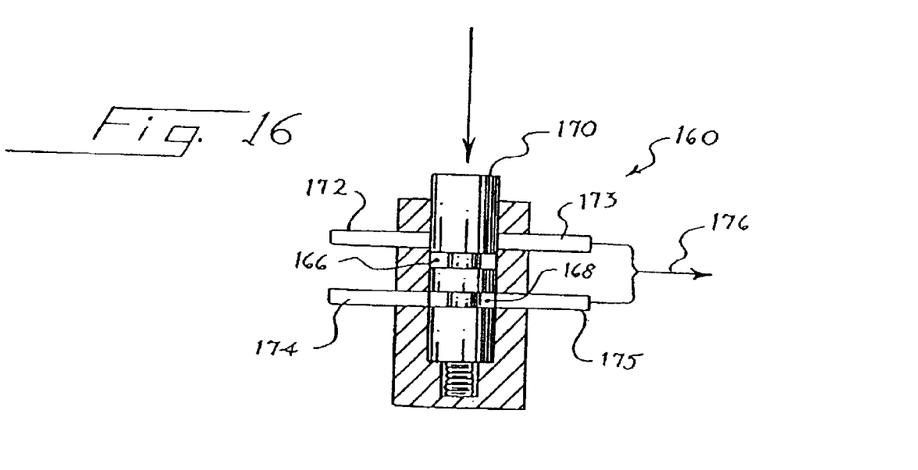

FIGS. 14, 15 and 16 provide three views of another modular valve assembly 160 that can be used as described above. As best shown in FIG. 14, the modular valve assembly 160 includes a housing 162 that supports a valve element 164 for sliding movement. The valve element 164 defines two spaced, annular recesses 166, 168, and the upper end of the valve element 164 forms an actuator 170. The valve element 164 is biased to the upper position shown in FIG. 14 by a spring 178.

The housing 162 supports first and second inlet ports 172, 174 and aligned tubes 173, 175 that are connected to an outlet port 176. The first inlet port 172 in use is connected to a liquid source, such as a source of irrigation fluid. The second inlet port 174 in use is connected to a suction source, such as a partial vacuum. The outlet port 176 in use is connected to an irrigation port of an endoscopic device. Check valves, not shown, may be used to prevent flow from the tube 173 to the tube 175 and vice-versa.

In the rest position of FIG. 14, the valve element 164 isolates both the first and second inlet ports 172, 174 from the outlet port 176. This is because the first inlet port 172 is out of alignment with the first recess 166, and the second inlet port 174 is out of alignment with the second recess 168.

FIG. 15 shows the valve assembly 160 in a second position, in which the user has depressed the actuator 170, thereby compressing the spring 178 and bringing the first recess 166 into alignment with the first inlet port 172 and the tube 173. In this position, irrigation fluid from the liquid source is passed by the assembly 160 to the outlet port 176.

As shown in FIG. 16, when the actuator 170 is further depressed, the first recess 166 is moved out of alignment with the first inlet port 172, and the second recess 168 is moved into alignment with the second inlet port 174. In this position, the valve assembly 160 allows suction from the suction source to pass via the second inlet port 174 and the second tube 175 to the outlet port 176.

The modular valve assembly 160 of FIGS. 14 through 16 is intended to be removably attached to the handpiece of an endoscopic device, all as described above. Any of the mechanisms described above for releasably securing the valve assembly to the handpiece can be used. The valve assembly 160 provides all of the functions described above regarding the valving of irrigation fluid from the liquid source to the outlet port 176. In addition, the valve assembly 160 allows the physician efficiently and easily to introduce suction to the endoscopic device by moving the actuator 170 to the fully depressed position of FIG. 16. Thus, a single valve assembly controls both the introduction of irrigation fluid and the application of suction to the irrigation port of the endoscopic device.

The valve assembly 160 utilizes a linear slide valve to implement the valving functions described above. It should of course be understood that this invention is not limited to such linear slide valves, and that the widest variety of valve mechanisms can be used to perform these valving functions.

Figure 17:
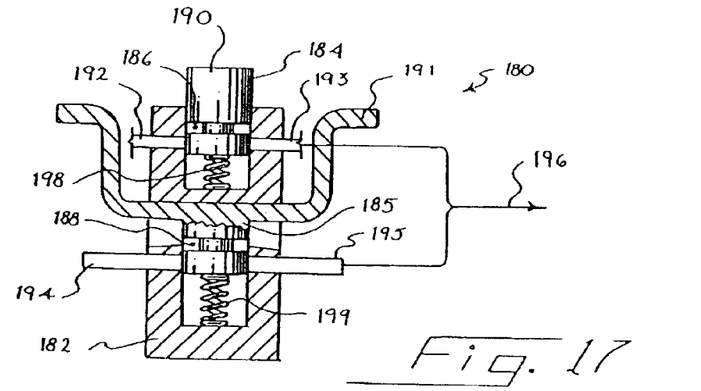
FIG. 17 is a sectional view of another modular valve assembly of this invention.

FIG. 17 shows a sectional view of another modular valve assembly 180 also intended to be releasably secured to the handpiece of an endoscopic device as described above. The modular valve assembly 180 includes a housing 182 that supports first and second valve elements 184, 185. The first valve element 184 includes a first recess 186 and a first actuator 190. The first valve element 184 is biased to the upper position shown in FIG. 17 by a spring 198. In this upper position the valve element 184 blocks the flow of liquid between a first inlet port 192 and a tube 193. As shown in FIG. 17, the tube 193 is coupled to an outlet port 196, which may in turn be coupled to an irrigation port of an endoscopic device as described above (not shown). When the first actuator 190 is depressed to bring the first recess 186 into alignment with the first inlet port 192 and the first tube 193, irrigation fluid from a liquid source (not shown) passes from the first inlet port 192 to the outlet port 196.

The second valve element 185 defines a second recess 188 and is biased to an upper position as shown in FIG. 17 by a second spring 199. The upper portion of the second valve element 185 is coupled to a second actuator 191. In this non-limiting example, the second actuator 191 is arranged so that the physician can reach it from any side of the valve assembly 180. This can be accomplished by forming the upper portion of the actuator 191 as a ring that encircles the housing 182. Alternatively, the actuator 191 may include a swivel, not shown, that allows the physician to rotate the upper portion of the actuator 191 to a desired angular position relative to the lower portion of the actuator 191 about an axis parallel to the sliding motion of the second valve element 185. In the rest position shown in FIG. 17, the second valve element 185 blocks the flow of suction from a second inlet port 194 to the tube 195 (which is in turn coupled to the outlet port 196). When the user depresses the second actuator 191 to bring the second recess 188 into alignment with the second inlet port 194 and the second tube 195, suction is applied to the outlet port 196.

The modular valve assembly 180 is provided with adhesive straps, mechanical fasteners, spring clips or the like for releasably securing it to the handpiece of an endoscopic device (not shown). The modular valve assembly 180 allows the user to control the flow of irrigation fluid and the application of suction to the outlet port 196. In this case, the user moves his or her finger between the first and second actuators 190, 191 to provide irrigation fluid or suction to the outlet port 196, respectively.

Figures 18, 19, 20:
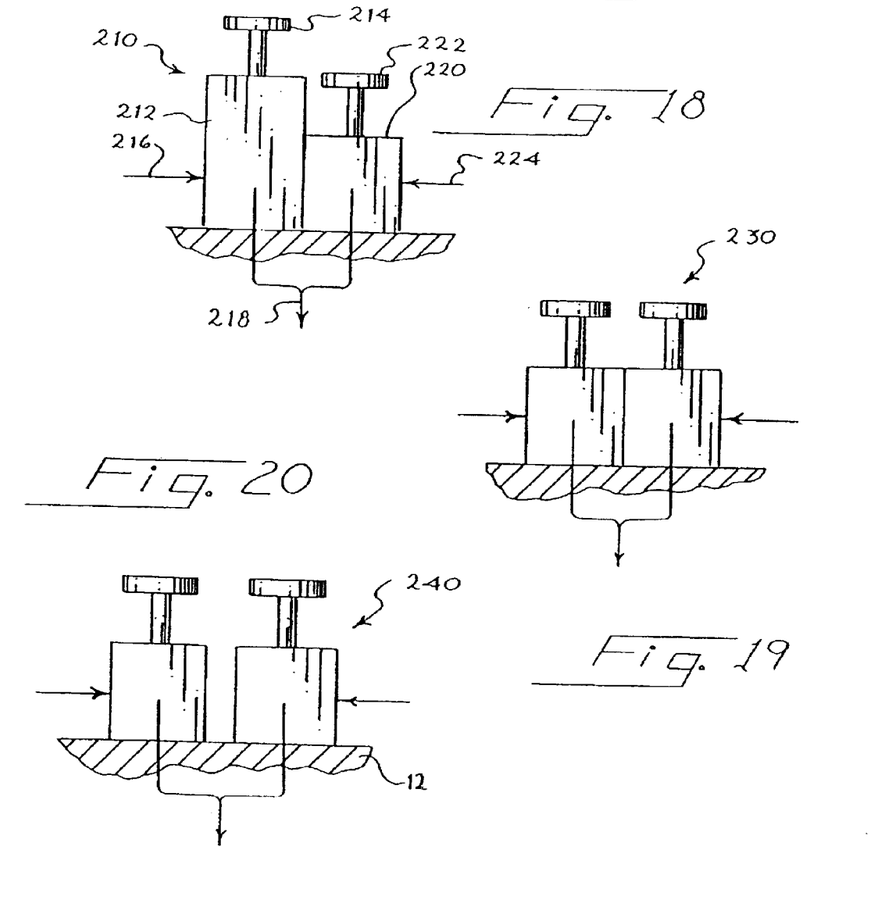
FIGS. 18, 19 and 20 are side views of three additional modular valve assemblies of this invention.

FIG. 18 shows another modular valve assembly 210 that performs all of the functions described above in conjunction with FIGS. 16 and 17. The modular valve assembly 210 includes a housing 212, 220 that supports two separate valves, each controlled by a respective actuator 214, 222. The actuator 214 controls the flow of irrigation fluid between a first Inlet port 216 and an outlet port 218, and the second actuator 222 controls the introduction of suction from the second inlet port 224 to the outlet port 218. In this case the actuators 214, 222 and the associated valves are positioned in side-by-side relationship, but at differing elevations to assist the user in discriminating between the two actuators 214, 222.

The modular valve assembly 230 of FIG. 19 is similar to the valve assembly 210, except that in this case the two actuators are positioned at the same elevation.

The modular valve assembly 240 of FIG. 20 is similar to the modular valve assembly 230, but in this case the two valves are mounted some distance from one another on the handpiece 12. FIG. 20 shows the manner in which a housing may include two or more spatially separated parts.

The modular valve assemblies of FIGS. 12 through 20 are all intended to be releasably mounted to an endoscopic device and to allow the user to control the flow of at least irrigation fluid to the irrigation port of the endoscopic device. The modular valve assemblies of FIGS. 14 through 20 additionally allow the user to control the application of suction to the irrigation port. The valve assemblies of FIGS. 14 through 20 are used in the same manner as the valves described above, except that the first inlet port 172, 192, 212 is connected to a source of irrigation fluid and the second inlet port 174, 194, 224 is connected to a source of suction prior to the surgical procedure. This can be done either before or after the modular valve assembly 160, 180, 210, 230, 240 is releasably mounted to the handpiece of the endoscopic device.

It should be apparent from the foregoing description that the improved modular valve assembly of this invention provides the important advantage that little or no modification is required to a conventional endoscope, yet the physician using the endoscope is provided with improved control over the flow of irrigation fluid. In particular, the physician can use direct finger pressure to modulate the flow of irrigation fluid as desired, while still leaving one hand free for surgical procedures. In this way, the need for a trained surgical nurse is reduced, and the physician's control over irrigation fluid flow is improved. The valve assembly described above is well suited for use with a wide variety of endoscopes including modern, small endoscopes that are too small for built-in valves.

Of course, it should be understood that a wide range of changes and modifications can be made to the preferred embodiments described above. For example, the valve of the valve assembly can take any suitable form, and it is not limited to the specific examples described above. The motion used to open or close the valve 36 can be varied as appropriate for the application, and it can include a lifting motion, a depressing motion, a sliding motion parallel to the length of the handpiece, or a rotating motion as desired. As a further alternative, the valve may be implemented as an element that pinches a resilient tube to slow or block flow through the tube. Thus, the valve can be implemented as a one-piece or a multiple-piece system having sliding, hinged, rotating or other motions.

Similarly, the mechanical fasteners that releasably hold the valve assembly in place on the handpiece of the endoscope can take any suitable form, and such fasteners are not limited to the adhesives, straps, snap-lock studs, and recesses described above. Many other mechanical fasteners can be adapted for use with this invention, as for example linear or rotary guides (including, e.g., dovetail guides or bayonet sockets) and various types of resilient or bendable elements that releasably hold the valve assembly in place.

Figure 21:
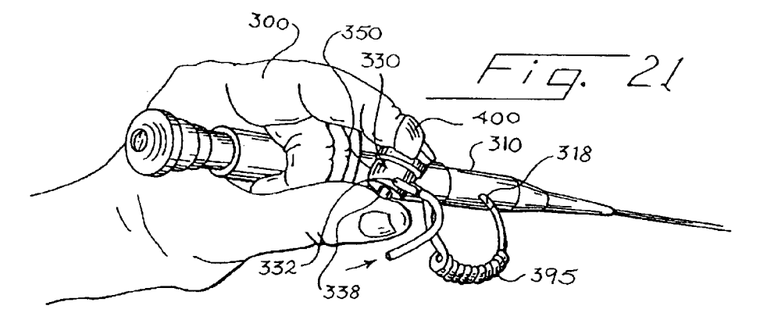
FIG. 21 is a perspective view showing an endoscope valve assembly releasably secured to an index finger of a hand holding an endoscope.
Figure 22:
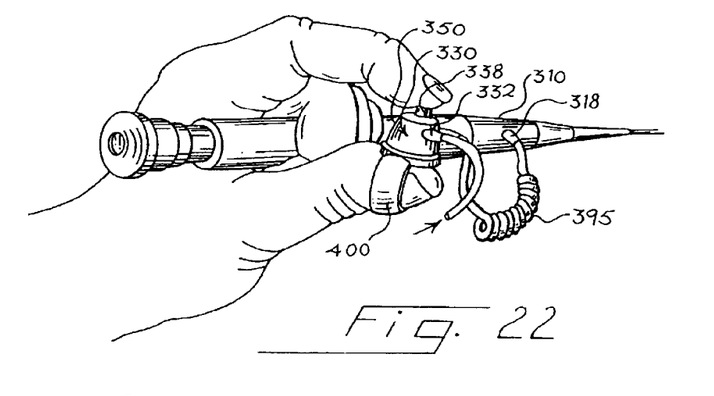
FIG. 22 is a perspective view showing an endoscope valve assembly releasably secured to a thumb of a hand holding an endoscope.
Figure 23:
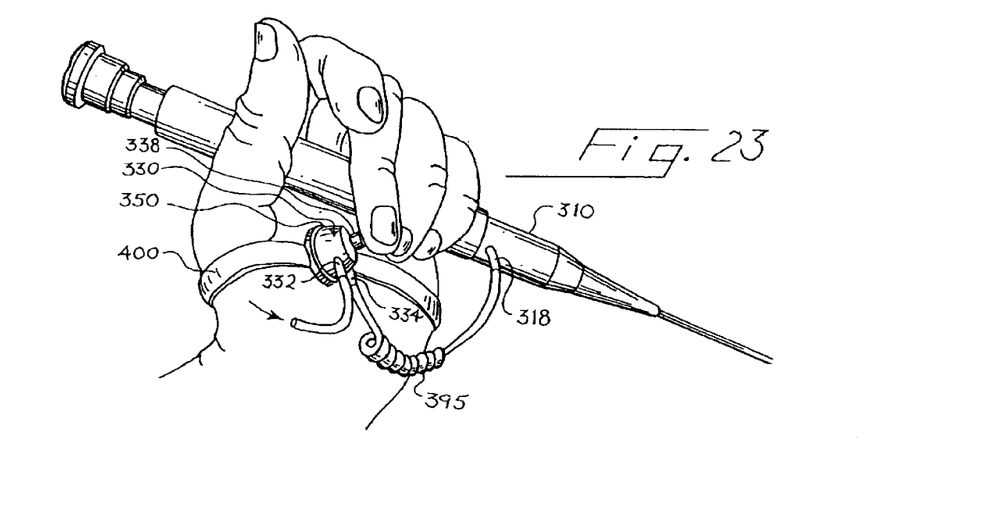
FIG. 23 is a perspective view showing an endoscope valve assembly releasably secured to a palm of a hand holding an endoscope.

In the embodiments described above, the valve assembly was releasably secured to the endoscope. In another embodiment, the valve assembly is releasably secured to a hand of a user using the endoscope instead of to the endoscope itself. FIGS. 21–23 show several illustrations of this embodiment. Like the valve assembly described previously, the valve assembly 330 of this embodiment comprises a housing 350, an inlet port 332, an outlet port 334, and a valve comprising a manually-controlled actuator 338. The inlet port 332 is connected with a source of pressurized or non-pressurized irrigation fluid, and the outlet port 334 of the valve assembly 330 is connected with the irrigation port 318 of the endoscope 310. In the illustrations shown in FIGS. 21–23, a coiled tubing 395 is used to connect the outlet port 334 of the valve assembly 330 with the irrigation port 318 of the endoscope 310. Because the tubing 395 is coiled, the valve assembly 330 can be located relatively close to the irrigation port 318 without excess tubing getting in the way of the user. Additionally, the coiled tubing 395 is expandable (like a telephone cord) to allow the valve assembly 330 to be located relatively far away from the irrigation port 318. Further, by being coiled, the tubing 395 is more kink resistant than non-coiled tubing.

The valve assembly 330 comprises a securing element 400 coupled with the housing 350 and operative to releasably secure the housing 350 to a hand of a user using the endoscope 310. In one implementation (shown in FIG. 24), the securing element 400 takes the form of a strap with hook-and-loop fasteners (e.g., a Velcro™ strap) that is secured to one side of the housing 350 in any suitable manner (e.g., glued, stitched, or riveted). The other side of the housing 350 contains a "D-loop" 410 through which the loose end of the strap 400 can be wrapped. One side of the strap 400 contains hooks, and the other side contains loops such that When the loose end of the strap 400 is wrapped around the D-loop 410, the strap 400 can secure to itself. In one implementation, the width of the strap 400 is about 1.5 cm wide.

In FIG. 21, the valve assembly 330 is releasably secured to the index finger of the user's hand 300, and the user moves the actuator 338 with his thumb. The design of the securing element 400 allows the valve assembly 330 to be releasably secured to other parts of the user's hand 300. For example, in FIG. 22, the valve assembly 330 is releasably secured to the user's thumb, and the actuator 338 is moved with the user's index finger. It should be noted that while FIGS. 21 and 22 show the valve assembly 330 being secured to a single digit, the valve assembly 330 can be secured to two or more digits. In FIG. 23, instead of being secured to a digit, the valve assembly 330 is releasably secured to the user's palm, and the actuator 338 is moved using one of the user's digits (here, a finger). FIGS. 21–23 show only some of the many possible positions of the valve assembly 330, and other positions are possible. For example, the valve assembly 330 can be secured to the user's finger, and the actuator can be moved by pressing the valve assembly 330 against the user's palm.

There are several advantages associated with securing the valve assembly to the user's hand instead of to the endoscope. Although the valve assembly of these embodiments can be releasably secured to a wide variety of endoscopes, it is contemplated that some endoscopes may not have the space or a convenient location for the valve assembly to secure to. By securing the valve assembly to the user's hand, the user can ensure that the valve assembly can be used with any type of endoscope and can be positioned in a location the user's finds convenient. Additionally, a user may not wish to use some types of securing elements with an endoscope. For example, a pressure-sensitive adhesive may leave an undesirable residue on an endoscope. Securing the valve assembly to the user's hand avoids this possible disadvantage.

In the illustrations shown in FIGS. 21–23, the valve assembly was secured to the same hand as that holding the endoscope. This allows the user to use a single hand to both hold the endoscope and to control the flow of irrigation fluid. In an alternate embodiment, the user holds the endoscope in one hand and releasably secures the valve assembly to his other hand. This allows the user to hold the endoscope in one hand and manually control the fluid flow with the other hand, which is typically used to manipulate surgical tools introduced into the patient via a working port in the endoscope. One such surgical tool is an endoscopic stone-destruction device (e.g., a destructive laser fiber), and another such tool is an endoscopic stone-extraction device. U.S. Pat. No. 6,419,679, which is by the same inventor as the present application and is hereby incorporated by reference, describes such devices. In another alternate embodiment, the valve assembly for the endoscope is releasably secured to the second medical instrument (such as the handle of an endoscopic stone-destruction or stone-extraction device) instead of to the hand of the user.

It should be noted that, although a strap with hook-and-loop fasteners was used in the illustrations in FIGS. 21–24, any other type of suitable securing element can be used such as the securing elements previously discussed (e.g., a pressure-sensitive adhesive, straps without hook-and-loop fasteners, resilient or bendable elements, etc.). Some specific examples within these general categories include, but are not limited to, a ring that fits over the user's digit, a stretchable band, a mechanical fastener secured to the valve assembly that engages with a mating fastener secured to the user's hand, elements that can be tied around the user's hand, a deformable material through which a user slides part of his hand (e.g., a digit) into and out of, magnets, etc. The securing element can also take the form of a digit sheath or glove that the user wears on his hand. As illustrated by these examples, the securing element can be a single- or multiple-piece design, can be continuous or broken, and can be made from a rigid or resilient material. Further, the type of securing element can be chosen such that the valve assembly can be secured to both the user's hand and to the endoscope (or to another medical instrument), thereby giving the user maximum flexibility in choosing where to position the valve assembly. Additionally, two (or more) securing elements can be used. For example, one securing element can be used to secure the valve assembly to the endoscope, and another securing element can be used to secure the valve assembly to the user's hand. Preferably, the securing element that is not used (e.g., the "hand" securing element) does not interfere with the securing element that is being used (e.g., the "endoscope" securing element).

Figures 24, 25:
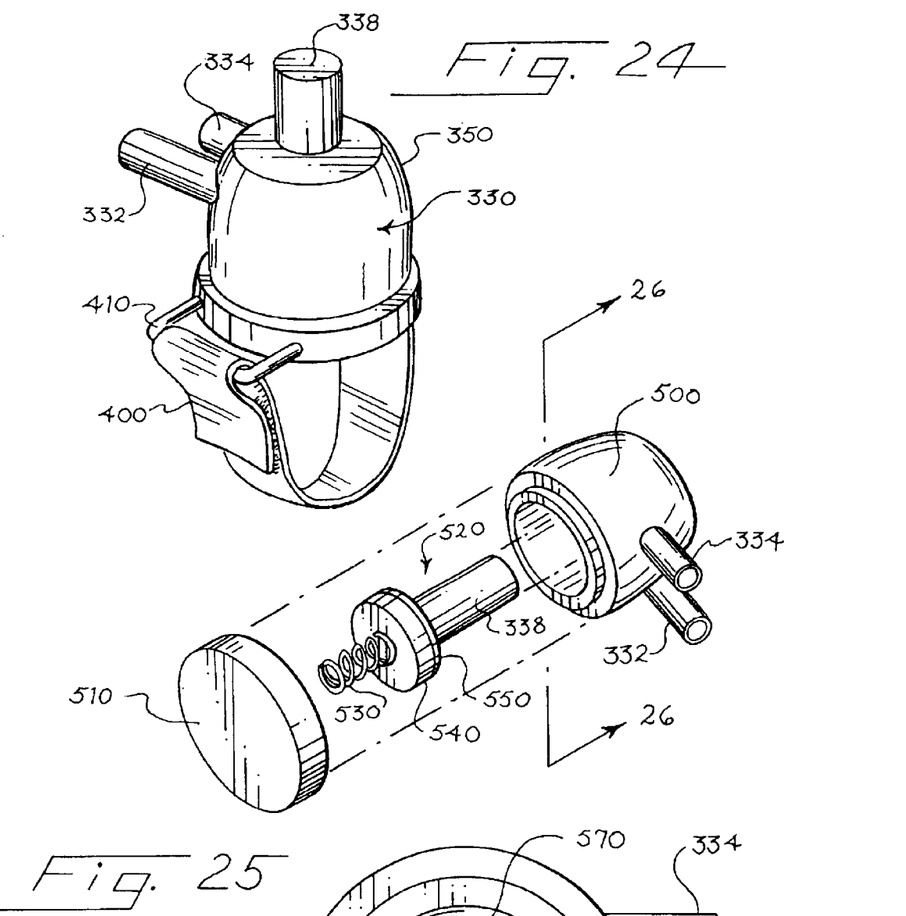
FIG. 24 is a perspective view of an endoscope valve assembly of one embodiment.
FIG. 25 is an exploded view of the endoscope valve assembly of FIG. 24.
Figure 26:
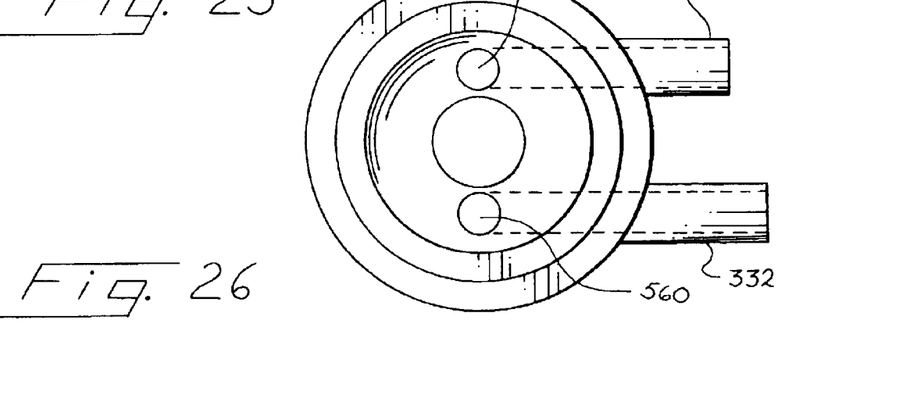
FIG. 26 is a sectional view taken along line 26-26 of FIG. 25.

Turning again to the drawings, FIGS. 25 and 26 are illustrations of one suitable valve design. FIG. 25 is an exploded view showing the components of the valve. The housing 330 comprises two parts; a cap 500 and a base 510. In this embodiment, the actuator 338 extends about 0.7 cm above the top of the housing 350 when assembled, the width of the actuator 338 is about 0.5 cm, and the housing 330 and the actuator 338 are made of plastic. Although not shown in FIG. 25, a rubber sponge can be placed on the bottom of the base 510 to (1) provide additional friction to help prevent the valve assembly 330 from slipping off the user's hand, (2) provide a comfortable surface for the user, and (3) prevent scratching of the endoscope 310 when the valve assembly 330 is secured to the endoscope 310 instead of to the user's hand.

The actuator 338 is part of a plunger-type component 520 comprising a spring 530, a disk 540, and a rubber gasket 550. As shown In FIG. 26, the top surface of the cap 550 contains two holes 560, 570. Hole 560 leads to the inlet port 332, and hole 570 leads to the outlet port 334. When assembled, the spring 530 biases the disk 540 and rubber gasket 550 against the top surface of the cap 500 and prevents flow between the inlet and outlet ports 332, 334. In this configuration, the actuator 338 is in a first position. When the user presses on the actuator 338, the actuator 338 moves to a second position, in which the disk 540 and rubber gasket 550 are spaced away from the holes 560, 570. This allows fluid to flow between the inlet and outlet ports 332, 334. When the user releases the actuator 338, the spring 530 returns the actuator 338 to the first position, and the disk 540 and rubber gasket 550 once again block flow between the inlet and outlet ports 332, 334.

It should be understood that other valve mechanisms can be used. Additionally, it is contemplated that other valve designs may provide advantages over the valve design shown in FIGS. 25 and 26. For example, it may be preferred to use a valve design that provides a graded flow (instead of a binary flow) so that the user can control the amount and rate at which the irrigant enters the endoscope (e.g., a few drops to full flow). To achieve this result, it may be preferred to use a valve design in which a blocking element moves past the inlet and/or outlet ports. Additionally, to provide a finer degree of control, it may be preferred to design the length of the actuator 338 to be more than 0.7 cm above the surface of the housing 350. Additionally, to reduce stress on the user's hand, it may be preferred to design the width of the actuator 338 to be more than 0.5 cm and to provide the actuator 338 with a smooth, comfortable surface. Further, it may be preferred to use a relatively-low spring resistance to allow the user to easily press the actuator 338.

It should also be understood that any of the embodiments previously described herein can be used in combination with the embodiments shown in FIGS. 21–26. For example, the valve assembly can be constructed with an additional inlet port for connection to a suction source. The same or second valve (with a second actuator) can be used to control suction flow. As another example, a latch mechanism, such as the ones conventionally used with retractable ballpoint pens, can be used to lock the actuator in a position at a full flow. Once the latch is engaged, the user can take his hand off the actuator, and high volume flow of irrigation fluid will be maintained from the inlet port to the outlet port. To stop the flow of irrigation fluid, the user again depresses the actuator, thereby causing the latch to release the actuator to move upwardly and stop the flow. This is only one example of a suitable latch, and many alternatives are possible.

As used herein, the term "position" is intended broadly to encompass a range of positions. Thus, the valve may block fluid flow between the inlet and outlet ports in a range of blocking positions and the valve may allow fluid to flow from the inlet port to the outlet port in a range of opened positions. The valve may be configured as an on/off valve or as a modulating valve.

The term "handpiece" is intended broadly to refer to the part of an endoscope that carries the eyepiece and is held by the user, whether referred to as the handpiece, the bridge, or by some other term by the manufacturer of the endoscope.

The term "housing" is intended broadly to include one-part housings as well as housings having two or more parts that may be physically integrated with one another or spatially separated from one another.

The term "valve" is intended broadly to encompass valves having one or more moveable valve elements controlling the flow of one or more fluids.

The term "inlet port" is intended broadly to refer to a port that is connected either to a fluid source or to a suction source.

The term "hand" refers to any part of the user's hand, such as the palm or digits.

The term "digit" refers to either one of the user's four fingers or to the user's thumb.

Also, any suitable structure can be used for pressurizing the irrigation liquid, including simple gravity feeds in some examples.

The foregoing detailed description has discussed only a few of the many forms that this invention can take. This detailed description is therefore intended by way of illustration and not by way of limitation. It is only the following claims, including all equivalents, that are intended to define the scope of this invention.

What is claimed is:

1. A method for enhancing control efficiency of a medical endoscope, the method comprising:
   (a) providing a medical endoscope comprising an irrigation port;
   (b) providing an endoscope valve assembly comprising:
      a housing comprising an inlet port and an outlet port;
      a valve carried by the housing and coupled between the inlet port and the outlet port, the valve comprising a manually-controlled actuator movable by a user using the endoscope between a first position, in which the valve blocks flow between the inlet port and the outlet port, and a second position, in which the valve allows flow between the inlet port and the outlet port; and
      a securing element;
   (c) releasably connecting the outlet port of the valve assembly with the irrigation port of the endoscope; and
   (d) releasably securing the securing element of the valve assembly at least partially around a hand of the user.

2. The invention of claim 1, wherein the valve assembly is releasably secured to a first digit of the user's hand, and wherein the user moves the manually-controlled actuator with a second digit of the user's hand.

3. The invention of claim 2, wherein the first digit comprises a finger, and wherein the second digit comprises a thumb.

4. The invention of claim 2, wherein the first digit comprises a thumb, and wherein the second digit comprises a finger.

5. The invention of claim 1, wherein the valve assembly is releasably secured to the user's palm, and wherein the user moves the manually-controlled actuator with a digit of the user's hand.

6. The invention of claim 1, wherein the valve assembly is releasably secured to a digit of the user's hand, and wherein the user moves the manually-controlled actuator with the user's palm.

7. The invention of claim 1, wherein the user holds the endoscope with the hand to which the valve assembly is releasably secured.

8. The invention of claim 1, wherein the user holds the endoscope with a hand other than the hand to which the valve assembly is releasably secured.

9. The invention of claim 1, wherein the outlet port of the valve assembly is connected with the irrigation port in (c) using coiled tubing.

10. A method for enhancing control efficiency of a medical endoscope, the method comprising:

(a) providing a medical endoscope comprising an irrigation port;

(b) providing an endoscope valve assembly comprising:
a housing comprising an inlet port and an outlet port; and
a valve carried by the housing and coupled between the inlet port and the outlet port, the valve comprising a manually-controlled actuator movable by a user using the endoscope between a first position, in which the valve blocks flow between the inlet port and the outlet port, and a second position, in which the valve allows flow between the inlet port and the outlet port;

(c) releasably connecting the outlet port of the valve assembly with the irrigation port of the endoscope; and (d) releasably securing the valve assembly to a hand of the user;

wherein the valve assembly is releasably secured to the user's hand in (d) with a strap comprising hook-and-loop fasteners.

11. The invention of claim 10, wherein the housing comprises a D-loop, wherein a first end of the strap is attached to the housing, and wherein the valve assembly is releasably secured to the user's hand in (d) by wrapping a second end of the strap through the D-loop.

12. A method for enhancing control efficiency of a medical endoscope, the method comprising:

(a) providing a medical endoscope comprising an irrigation port;

(b) providing an endoscope valve assembly comprising:
a housing comprising an inlet port and an outlet port; and
a valve carried by the housing and coupled between the inlet port and the outlet port, the valve comprising a manually-controlled actuator movable by a user using the endoscope between a first position, in which the valve blocks flow between the inlet port and the outlet port, and a second position, in which the valve allows flow between the inlet port and the outlet port;

(c) releasably connecting the outlet port of the valve assembly with the irrigation port of the endoscope; and (d) releasably securing the valve assembly to a hand of the user;

wherein the valve assembly is releasably secured to the user's hand in (d) with a resilient element.

13. A method for enhancing control efficiency of a medical endoscope, the method comprising:

(a) providing a medical endoscope comprising an irrigation port;

(b) providing an endoscope valve assembly comprising:
a housing comprising an inlet port and an outlet port; and
a valve carried by the housing and coupled between the inlet port and the outlet port, the valve comprising a manually-controlled actuator movable by a user using the endoscope between a first position, in which the valve blocks flow between the inlet port and the outlet port, and a second position, in which the valve allows flow between the inlet port and the outlet port;

(c) releasably connecting the outlet port of the valve assembly with the irrigation port of the endoscope; and (d) releasably securing the valve assembly to a hand of the user;

wherein the valve assembly is releasably secured to the user's hand in (d) with a pressure-sensitive adhesive.

14. A method for enhancing control efficiency of a medical endoscope, the method comprising:

(a) providing a medical endoscope comprising an irrigation port;

(b) providing an endoscope valve assembly comprising:
a housing comprising an inlet port and an outlet port; and
a valve carried by the housing and coupled between the inlet port and the outlet port, the valve comprising a manually-controlled actuator movable by a user using the endoscope between a first position, in which the valve blocks flow between the inlet port and the outlet port, and a second position, in which the valve allows flow between the inlet port and the outlet port;

(c) releasably connecting the outlet port of the valve assembly with the irrigation port of the endoscope; and (d) releasably securing the valve assembly to a hand of the user;

wherein the valve assembly carries at least one of the following: a finger sheath or glove.

15. The invention of claim 1, wherein the actuator is mounted to slide linearly between the first and second positions.

16. The invention of claim 1, wherein the actuator is mounted to rotate between the first and second positions.

17. The invention of claim 1, wherein the valve assembly further comprises a latch coupled with the valve and operative to releasably hold the valve in a selected state in response to a control input by the user.

18. The invention of claim 17, wherein the latch is coupled to the actuator and operative to hold the valve in a state that allows flow between the inlet port and the outlet port in response to user manipulation of the actuator.

19. The invention of claim 1, wherein the housing further comprises a second inlet port, wherein the valve blocks flow between the second inlet port and the outlet port in the first and second positions, and wherein the actuator is movable by the user to a third position, in which the valve allows flow between the second inlet port and the outlet port while blocking flow between the first-mentioned inlet port and the outlet port.

20. The invention of claim 19 further comprising:
connecting the first-mentioned inlet port to a liquid source; and
connecting the second inlet port to a suction source.

21. The invention of claim 1, wherein the valve assembly further comprises:
a second inlet port included in the housing; and
a second valve carried by the housing and coupled between the second inlet port and the outlet port, the second valve comprising a manually-controlled second actuator movable by the user between a third position, in which the second valve blocks flow between the second inlet port and the outlet port, and a fourth position, in which the second valve allows flow between the second inlet port and the outlet port.

22. The invention of claim 21 further comprising:
connecting the first-mentioned inlet port to a liquid source; and
connecting the second inlet port to a suction source.

23. The invention of claim 1 wherein the endoscope comprises a ureteroscope.

24. A method for enhancing control efficiency of a medical endoscope, the method comprising:
(a) providing a medical endoscope comprising an irrigation port;
(b) providing a second medical instrument, wherein the second medical instrument has a different shape than the shape of the endoscope;
(c) releasably securing an endoscope valve assembly to the second medical instrument, the valve assembly comprising:
a housing comprising an inlet port and an outlet port; and
a valve carried by the housing and coupled between the inlet port and the outlet port, the valve comprising a manually-controlled actuator movable by a user between a first position, in which the valve blocks flow between the inlet port and the outlet port, and a second position, in which the valve allows flow between the inlet port and the outlet port;
(d) releasably connecting the outlet port of the valve assembly with the irrigation port of the endoscope;
(e) holding the medical endoscope with the user's first hand;
(f) holding the second medical instrument with the user's second hand; and
(g) using the user's second hand to move the manually-controlled actuator.

25. The invention of claim 24, wherein the second medical instrument comprises an endoscopic stone-extraction device.

26. The invention of claim 24, wherein the second medical instrument comprises an endoscopic stone-destruction device.

27. A modular endoscope valve assembly comprising:
a housing comprising an inlet port and an outlet port;
a securing element coupled with the housing, wherein the securing element is operative to releasably secure at least partially around a hand of a user using a medical endoscope; and
a valve carried by the housing and coupled between the inlet port and the outlet port, the valve comprising a manually-controlled actuator movable by a user between a first position, in which the valve blocks flow between the inlet port and the outlet port, and a second position, in which the valve allows flow between the inlet port and the outlet port.

28. A modular endoscope valve assembly comprising:
a housing comprising an inlet port and an outlet port;
a securing element coupled with the housing, wherein the securing element is operative to releasably secure the housing to a hand of a user using a medical endoscope; and
a valve carried by the housing and coupled between the inlet port and the outlet port, the valve comprising a manually-controlled actuator movable by a user between a first position, in which the valve blocks flow between the inlet port and the outlet port, and a second position, in which the valve allows flow between the inlet port and the outlet port;
wherein the securing element comprises a strap comprising hook-and-loop fasteners.

29. The invention of claim 28, wherein the housing comprises a D-loop, wherein a first end of the strap is attached to the housing, and wherein a second end of the strap wraps through the D-loop to secure the valve assembly to the user's hand.

30. A modular endoscope valve assembly comprising:
a housing comprising an inlet port and an outlet port;
a securing element coupled with the housing, wherein the securing element is operative to releasably secure the housing to a hand of a user using a medical endoscope; and
a valve carried by the housing and coupled between the inlet port and the outlet port, the valve comprising a manually-controlled actuator movable by a user between a first position, in which the valve blocks flow between the inlet port and the outlet port, and a second position, in which the valve allows flow between the inlet port and the outlet port;
wherein the securing element comprises a resilient element.

31. A modular endoscope valve assembly comprising:
a housing comprising an inlet port and an outlet port;
a securing element coupled with the housing, wherein the securing element is operative to releasably secure the housing to a hand of a user using a medical endoscope; and
a valve carried by the housing and coupled between the inlet port and the outlet port, the valve comprising a manually-controlled actuator movable by a user between a first position, in which the valve blocks flow between the inlet port and the outlet port, and a second position, in which the valve allows flow between the inlet port and the outlet port;
wherein the securing element comprises a pressure-sensitive adhesive.

32. A modular endoscope valve assembly comprising:
a housing comprising an inlet port and an outlet port;
a securing element coupled with the housing, wherein the securing element is operative to releasably secure the housing to a hand of a user using a medical endoscope; and
a valve carried by the housing and coupled between the inlet port and the outlet port, the valve comprising a manually-controlled actuator movable by a user between a first position, in which the valve blocks flow between the inlet port and the outlet port, and a second position, in which the valve allows flow between the inlet port and the outlet port;
wherein the securing element comprises a mechanical fastener.

33. The invention of claim 27, wherein the actuator is mounted to slide linearly between the first and second positions.

34. The invention of claim 27, wherein the actuator is mounted to rotate between the first and second positions.

35. The invention of claim 27, wherein the valve assembly further comprising a latch coupled with the valve and operative to releasably hold the valve in a selected state in response to a control input by the user.

36. The invention of claim 35, wherein the latch is coupled to the actuator and operative to hold the valve in a state that allows flow between the inlet port and the outlet port in response to user manipulation of the actuator.

37. The invention of claim 27, wherein the housing further comprises a second inlet port, wherein the valve blocks flow between the second inlet port and the outlet port in the first and second positions, and wherein the actuator is movable by the user to a third position, in which the valve allows flow between the second inlet port and the outlet port while blocking flow between the first-mentioned inlet port and the outlet port.

38. The invention of claim 37, wherein the first-mentioned inlet port is connected to a liquid source, and wherein the second inlet port is connected to a suction source.

39. The invention of claim 27, wherein the valve assembly further comprises:
- a second inlet port included in the housing;
- a second valve carried by the housing and coupled between the second inlet port and the outlet port, the second valve comprising a manually controlled second actuator movable by the user between a third position, in which the second valve blocks flow between the second inlet port and the outlet port, and a fourth position, in which the second valve allows flow between the second inlet port and the outlet port.

40. The invention of claim 39, wherein the first-mentioned inlet port is connected to a liquid source, and wherein the second inlet port is connected to a suction source.

41. The invention of claim 27, wherein the outlet port of the valve assembly is connected with the irrigation port of the endoscope with coiled tubing.

42. The invention of claim 27 wherein the endoscope comprises a ureteroscope.

43. The invention of claim 27, wherein the securing element is further operative to releasably secure the valve assembly to the endoscope.

44. The invention of claim 27, wherein the securing element is further operative to releasably secure the valve assembly to a second medical instrument held in the user's second hand.

45. The invention of claim 44, wherein the second medical instrument comprises an endoscopic stone-extraction device.

46. The invention of claim 44, wherein the second medical instrument comprises an endoscopic stone-destruction device.

* * * * *